United States Patent [19]

Melzer

[11] Patent Number: 5,502,388

[45] Date of Patent: Mar. 26, 1996

[54] METHOD OF MEASURING THE PH VALUE OF A TEST SOLUTION WITH GLASS-ELECTRODE MEASURING CELLS AND OF SIMULTANEOUSLY CALIBRATING THE MEASURING CELLS

[75] Inventor: Werner Melzer, Liederbach, Germany

[73] Assignee: Hoechst Aktiengesellschaft, Germany

[21] Appl. No.: 190,600

[22] Filed: Feb. 2, 1994

[30] Foreign Application Priority Data

Feb. 4, 1993 [DE] Germany .............. 43 03 187.0
Aug. 10, 1993 [DE] Germany .............. 43 26 764.5

[51] Int. Cl.⁶ .......................................... G01N 27/416
[52] U.S. Cl. ........................................ 324/438; 204/406
[58] Field of Search ................................ 324/438, 601; 73/1 R; 204/406–408

[56] References Cited

U.S. PATENT DOCUMENTS

| | | | |
|---|---|---|---|
| 3,405,048 | 10/1968 | Soltz | 324/438 |
| 3,662,256 | 5/1972 | Eckfeldt | 324/438 |
| 3,862,895 | 1/1975 | King et al. | |
| 4,406,766 | 9/1983 | MacDonald | 324/438 |
| 4,440,619 | 4/1984 | Daroczy et al. | |
| 4,506,226 | 3/1985 | Luce | 324/438 |
| 4,511,660 | 4/1985 | Lubbers et al. | 324/438 |
| 4,650,562 | 3/1987 | Harman | 324/438 |
| 4,713,618 | 12/1987 | Carlson et al. | 324/438 |
| 5,268,852 | 12/1993 | Forsythe et al. | 364/486 |

FOREIGN PATENT DOCUMENTS

| | | | |
|---|---|---|---|
| 0060533 | 9/1982 | European Pat. Off. | |
| 0080753 | 6/1983 | European Pat. Off. | 324/438 |
| 2617045 | 10/1977 | Germany. | |
| 0154351 | 9/1984 | Japan | 324/438 |
| 9217775 | 10/1992 | WIPO | 324/438 |

*Primary Examiner*—Maura K. Regan
*Attorney, Agent, or Firm*—Curtis, Morris & Safford

[57] ABSTRACT

In the method of measuring the pH value of a test solution with glass-electrode measuring cells and of simultaneously calibrating the measuring cells, the potentials occurring at the pH glass electrode and the reference electrode are processed in a pH meter with temperature compensation and measuring-cell slope derivation. The potentials from a reference electrode (4) and two pH glass electrodes (2, 3) having different internal reference solutions (6, 7) are processed in a first (8) and a second pH meter (9). The measuring-cell slope is derived from the processed potential and, together with the slope, the measured value is derived simultaneously.

5 Claims, 3 Drawing Sheets

METHOD OF MEASURING THE PH VALUE OF A TEST SOLUTION WITH GLASS-ELECTRODE MEASURING CELLS AND OF SIMULTANEOUSLY CALIBRATING THE MEASURING CELLS

TITLE OF THE INVENTION

Method of measuring the pH value of a test solution with glass-electrode measuring cells and of simultaneously calibrating the measuring cells.

BACKGROUND OF THE INVENTION

The invention relates to a method of measuring the pH value of a test solution with glass-electrode measuring cells and of simultaneously calibrating the measuring cells, in which method the potentials occurring at the pH glass electrode and the reference electrode are processed in a pH meter with temperature compensation and measuring-cell slope derivation.

Whereas the measuring-cell zero point of modern pH measuring cells remains largely stable, the measuring-cell slope has to be calibrated at certain intervals of time. For this purpose, the measuring cells are removed from the container, the continuous-flow vessel or pipe and calibrated externally in known buffers (calibrating solutions). In this process, the measuring-cell data, such as measuring-cell zero point and measuring-cell slope, are determined and their deviations compensated for in the pH meter. The calibration operation can often not be carried out at the processing temperatures but only at room temperature. For this reason, and also because of the costs associated therewith, a frequent calibration, for example to increase the measuring accuracy, generally has to be dispensed with.

It is furthermore known to withdraw the measuring cells pneumatically from the test solution and expose them to rinsing solutions and calibrating solutions. The deviations in the measuring-cell parameters found in this process are compensated for in the pH meter. Such systems are relatively complex and expensive. Problems are presented, in particular, by the wear associated with the pneumatic movement of the measuring cell and the satisfactory sealing of the measuring liquid, i.e. its retention in the container.

SUMMARY OF THE INVENTION

The invention avoids these disadvantages. The measuring cell always remains in the fixed position of the measuring point.

The invention achieves the object by a method of the type mentioned at the outset, wherein the potentials from a reference electrode and two pH glass electrodes having different internal reference solutions, are processed in a first and a second pH meter and the measuring-cell slope is derived from the processed potentials and, together with the slope, the measured value is derived simultaneously.

Suitable for carrying out the method is a pH measuring cell comprising a reference electrode and a pH glass electrode, wherein the measuring cell comprises:

a) a first pH glass electrode containing a first internal reference solution and connected, together with the reference electrode, to a first pH meter, and b) a second pH glass electrode containing a second internal reference solution and connected, together with the reference electrode, to a second pH meter.

In an alternative embodiment of the measuring cell, the electrode space of the glass electrode can be subdivided into two spaces by a partition and each space provided with a reference electrode and an internal reference solution. The partition may comprise a glass tube which is disposed in the electrode space of the glass electrode and subdivides it into two spaces which each contain a working electrode and different internal reference solutions and are sealed by a glass membrane.

The advantages of the invention are essentially to be seen in the fact that the measuring-cell slope, the most important parameter, can be calibrated simultaneously with the derivation of the measured value without removing the measuring cell, that is to say at the measuring point itself, and without replacing the internal reference solution. The calibration takes place at the product temperature prevailing at the time. The expenditure on control or evaluation of the calibration operation is low.

BRIEF DESCRIPTION OF THE DRAWINGS

The invention is explained in greater detail below by reference to exemplary embodiment figures. In the figures

DESCRIPTION OF THE PREFERRED EMBODIMENTS

Figure 1:
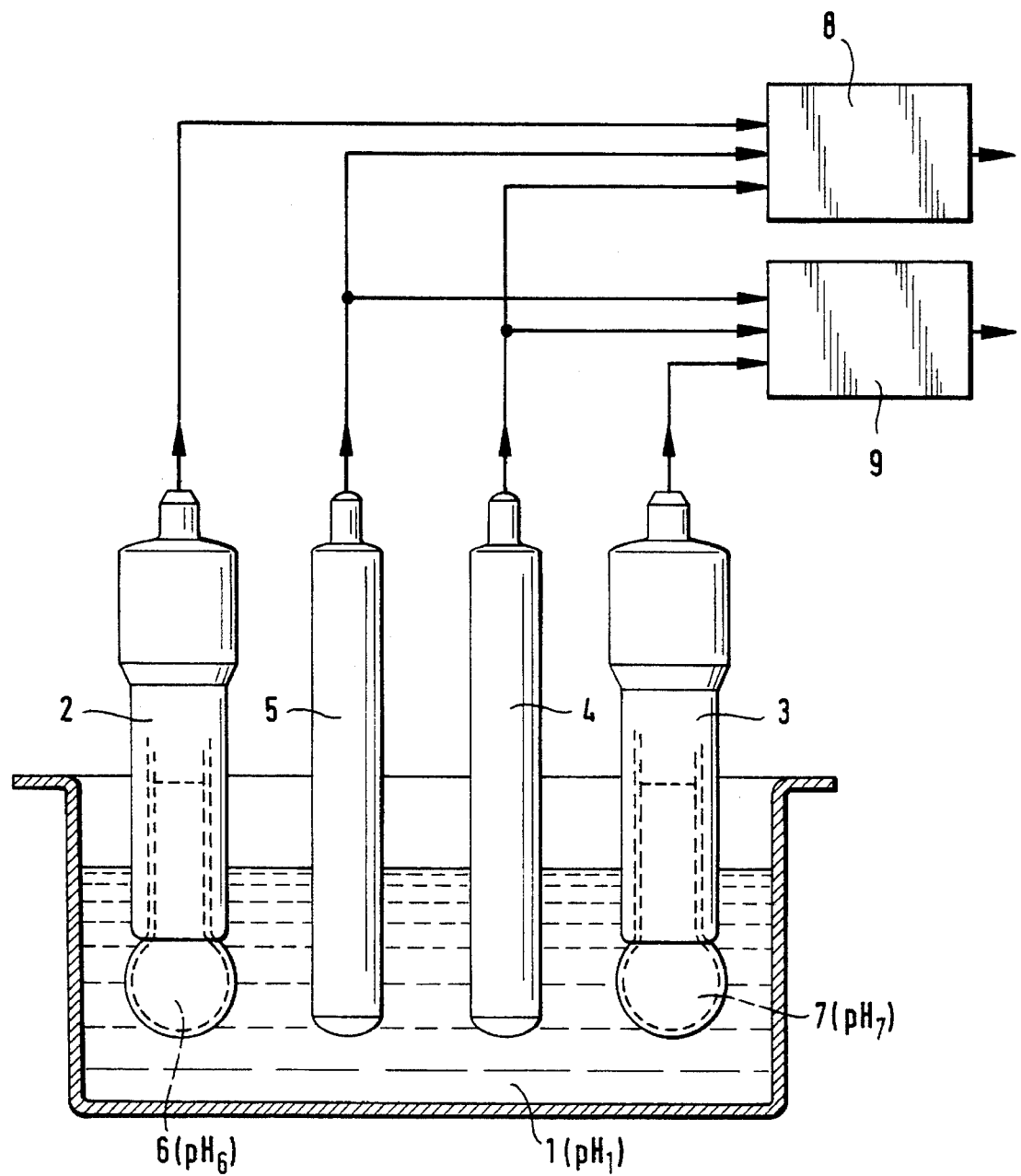
FIG. 1 shows a circuit diagram and the measuring cell for carrying out the method.

Disposed in the test solution I having the unknown pH value $pH_1$ are two pH glass electrodes 2 and 3, a reference electrode 4 and a temperature sensor 5. The glass electrodes 2 and 3 have different internal reference solutions 6 and 7 having known pH values $pH_6$ and $pH_7$ in each case. The glass electrode 2 is connected, together with the reference electrode 4 to the pH meter 8 and the glass electrode 3 is connected, together with the reference electrode 4 to the pH meter 9. Both pH meters are provided with a temperature compensation. The measuring-cell slope and, simultaneously with the slope, the measured value, i.e. the pH value of the test solution are derived from the potentials from the glass electrode and the reference electrode which are processed in the pH meters 8 and 9. The measuring-cell slope is the quotient of the difference in the measured potentials and the difference in the known pH values $pH_6$ and $pH_7$ of the internal reference solutions 6 and 7. If pH glass measuring cells are used in which the individual glass electrodes have different slopes, the potential of one of the pH glass electrodes is divided by the quotient which is derived from the individual slopes of the pH glass electrodes at room temperature. Impermissible changes can be immediately noticed and corrected in the pH meter with the ongoing determination of the measuring-cell slope, which is independent of changes in the pH value of the test solution if the state of the cell is in good order. To derive the measured value, either the potential processed in the pH meter 8 or that processed in the pH meter 9 can be used. The potentials processed in both the pH meters may also be used. The signals originating from the pH meters may also be monitored for consistency of the pH values of the test solution (partial redundancy). Preferably, the pH values of the internal reference solutions 6 and 7 are adjusted so that $pH_6 < pH_1 < pH_7$ or $pH_6 > pH_1 > pH_7$. An impermissible decrease in the measuring-cell slope of one or even both the measuring cells is thus detected particularly early.

Figure 2:
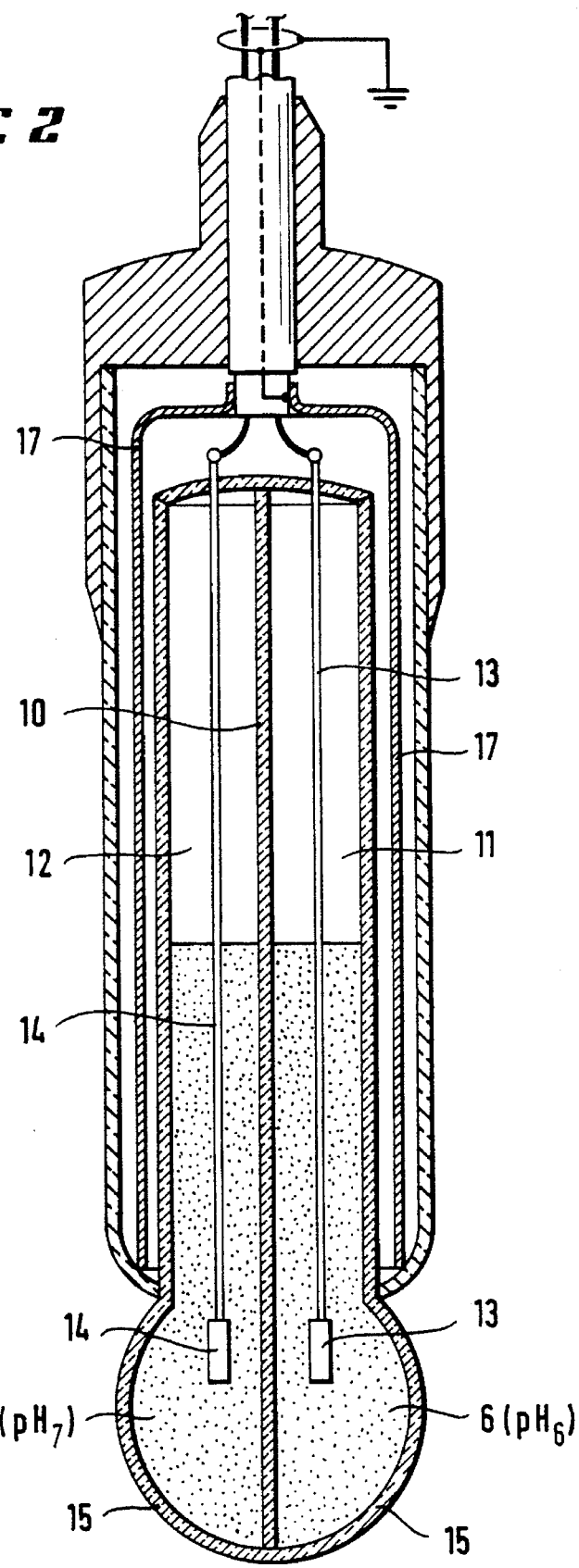
FIG. 2 shows a glass electrode for carrying out the method and FIG. 3 shows a portion of an alternative embodiment of the glass electrode.
Figure 3:
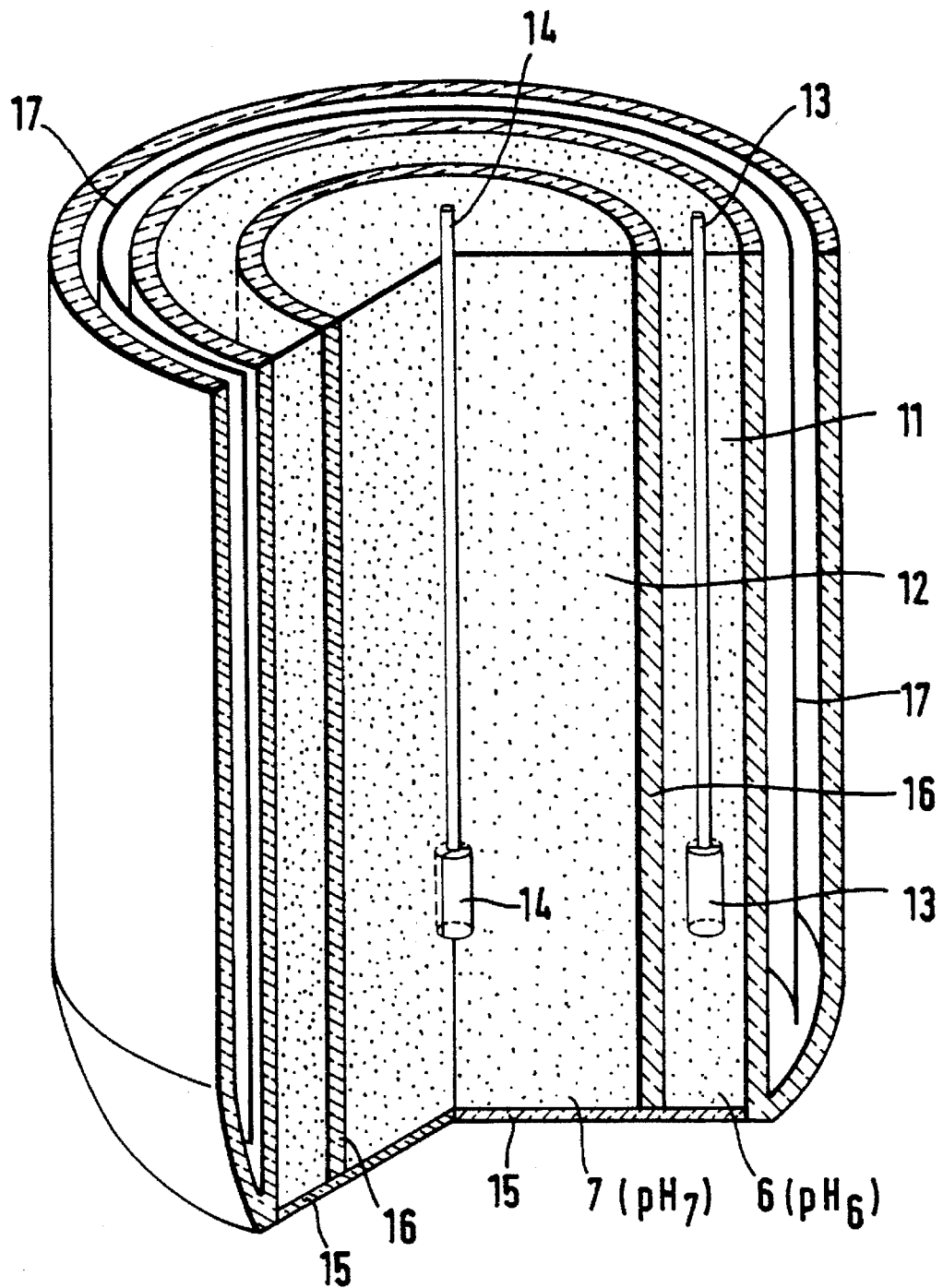

In the pH glass electrodes shown in FIG. 2, the electrode space is subdivided into two spaces (11, 12) by a partition (10). Each space (11, 12) is provided with a reference electrode (13, 14) and an internal reference solution (6, 7). The spaces (11, 12) are sealed by a glass membrane (15). In the embodiment shown in FIG. 3, the partition comprises a glass tube (16) which is disposed concentrically in the electrode space of the glass electrode and subdivides it into two spaces (11, 12) which are sealed by the glass membrane (15). (17) indicates the screen, which is grounded.

I claim:

1. A method of measuring the pH value of a test solution with glass-electrode measuring cells, in which method the potentials occurring between the glass-electrodes and a reference electrode are processed in pH meters with temperature compensation and measuring-cell slope deviation, wherein the potential between a first glass electrode and the reference electrode and the potential between a second glass electrode and the reference electrode, both glass electrodes having different internal reference solutions, are processed in a first pH meter and a second pH meter, wherein the measuring cell slope in said first pH meter and said second pH meter is derived from the processed potentials by dividing the difference in the processed potentials by the difference in the pH values of said internal reference solutions of said first glass electrode and said second glass electrode, and wherein the pH value of the test solution is derived from one of the processed potentials, the corresponding pH values of the internal reference solution and the derived measuring cell slope.

2. The method as claimed in claim 1, wherein one of the processed potentials is divided by the quotient which is derived from the individual slopes of the glass electrodes at room temperature.

3. A measuring cell for measuring the pH value of a test solution and for simultaneously calibrating the measuring cell slope by the method of claim 1, comprising pH glass electrodes and a reference electrode, wherein the measuring cell comprises:

a) a first pH glass electrode containing a first internal reference solution and connected, together with the reference electrode, to a first pH meter, and b) a second pH glass electrode containing a second internal reference solution and connected, together with the reference electrode, to a second pH meter.

4. A pH glass electrode for measuring the pH value of a test solution by the method of claim 1, wherein an inner space of the glass electrode is subdivided into two spaces by a partition and each space is provided with a reference electrode and an internal reference solution and is sealed from a test solution by a common pH-sensitive glass membrane.

5. The pH glass electrode as claimed in claim 4, wherein the partition comprises a glass tube which is disposed concentrically in the inner space of the glass electrode.

* * * * *

UNITED STATES PATENT AND TRADEMARK OFFICE
CERTIFICATE OF CORRECTION

PATENT NO. : 5,502,388
DATED : March 26, 1996
INVENTOR(S) : Werner Melzer

It is certified that error appears in the above-identified patent and that said Letters Patent is hereby corrected as shown below:

Claim 1, line 5, change "deviation" to --derivation--.

Signed and Sealed this

Eighteenth Day of March, 1997

Attest:

BRUCE LEHMAN

Attesting Officer

Commissioner of Patents and Trademarks